US008757991B2

(12) United States Patent
Maitre et al.

(10) Patent No.: US 8,757,991 B2
(45) Date of Patent: Jun. 24, 2014

(54) PERISTALTIC PUMP AND INSERTABLE IRRIGATION LINE WITH A TUBE PORTION HAVING A DETERMINED PROFILE

(75) Inventors: Luc Maitre, Epauvillers (CH); Cyril Ryser, Tramelan (CH); Laurent Farine, Moutier (CH); Didier Siegenthaler, Cornaux (CH)

(73) Assignee: Bien-Air Holding S.A., Bienne (CH)

( * ) Notice: Subject to any disclaimer, the term of this patent is extended or adjusted under 35 U.S.C. 154(b) by 371 days.

(21) Appl. No.: 13/002,496

(22) PCT Filed: Jun. 29, 2009

(86) PCT No.: PCT/EP2009/058120
§ 371 (c)(1),
(2), (4) Date: Mar. 23, 2011

(87) PCT Pub. No.: WO2010/000702
PCT Pub. Date: Jan. 7, 2010

(65) Prior Publication Data
US 2011/0165005 A1    Jul. 7, 2011

(30) Foreign Application Priority Data
Jul. 3, 2008   (EP) ..................................... 08159641

(51) Int. Cl.
*F04B 43/12*   (2006.01)
(52) U.S. Cl.
USPC .................................. 417/477.2; 417/477.11
(58) Field of Classification Search
USPC ................ 417/476, 477.1, 477.2, 473, 477.4, 417/477.5, 477.7, 477.8, 477.6, 477.9, 417/477.11, 477.12
See application file for complete search history.

(56) References Cited

U.S. PATENT DOCUMENTS

| 2,035,159 A | * | 3/1936 | Henry ........................... 417/476 |
| 3,963,023 A | * | 6/1976 | Hankinson ...................... 604/19 |
| 4,187,057 A | * | 2/1980 | Xanthopoulos ................. 417/63 |
| 4,537,561 A | * | 8/1985 | Xanthopoulos ................. 417/63 |

(Continued)

FOREIGN PATENT DOCUMENTS

| EP | 1 400 691 A2 | 3/2004 |
| GB | 2 012 373 A | 7/1979 |

OTHER PUBLICATIONS

European Search Report issued in corresponding European Application No. PCT/EP2009/058120, completed Sep. 24, 2009, mailed Oct. 5, 2009.

*Primary Examiner* — Devon Kramer
*Assistant Examiner* — Nathan Zollinger
(74) *Attorney, Agent, or Firm* — Griffin & Szipl, P.C.

(57) ABSTRACT

A flexible tube portion for an irrigation line connected to a supply of fluid for surgical or dental use is disclosed, wherein the flexible tube portion cooperates with rollers of a peristaltic pump for distributing fluid, which includes a particular structure which, between two free ends thereof, define a distance, which, combined with the length of the tube portion, gives the tube portion a determined profile enabling its positioning directly underneath the raceway of the rollers of the pump. Also disclosed is a peristaltic pump including a plurality of rollers that roll over a flexible tube portion of an irrigation line connected to a supply of fluid for surgical or dental use, which includes a certain structure for receiving the flexible tube portion in front of the plane in which the rollers move, then bringing the flexible tube portion underneath the rollers, and pressing the tube portion against the rollers.

13 Claims, 12 Drawing Sheets

(56) References Cited

U.S. PATENT DOCUMENTS

| | | | |
|---|---|---|---|
| 4,599,055 A * | 7/1986 | Dykstra | 417/477.2 |
| 5,267,956 A * | 12/1993 | Beuchat | 604/30 |
| 5,273,517 A * | 12/1993 | Barone et al. | 494/37 |
| 5,433,588 A * | 7/1995 | Monk et al. | 417/477.2 |
| 5,460,490 A * | 10/1995 | Carr et al. | 417/44.2 |
| 5,588,815 A * | 12/1996 | Zaleski, II | 417/477.2 |
| 5,676,530 A * | 10/1997 | Nazarifar | 417/360 |
| 5,759,017 A * | 6/1998 | Patton et al. | 417/477.9 |
| 5,927,956 A * | 7/1999 | Lim et al. | 417/477.13 |
| 6,109,895 A * | 8/2000 | Ray et al. | 417/477.2 |
| 6,468,059 B2 * | 10/2002 | Haser et al. | 417/477.1 |
| 6,731,216 B2 * | 5/2004 | Ho et al. | 340/608 |
| 7,018,182 B2 * | 3/2006 | O'Mahony et al. | 417/476 |
| 7,273,359 B2 * | 9/2007 | Blight et al. | 417/477.13 |
| 7,959,196 B2 * | 6/2011 | Dale | 292/303 |
| 8,272,857 B2 * | 9/2012 | Norman et al. | 417/474 |
| 2005/0069419 A1 | 3/2005 | Cull et al. | |
| 2005/0254978 A1 * | 11/2005 | Huber et al. | 417/477.1 |
| 2007/0212240 A1 * | 9/2007 | Voyeux et al. | 417/477.2 |
| 2007/0217933 A1 * | 9/2007 | Haser et al. | 417/477.2 |
| 2007/0258838 A1 * | 11/2007 | Drake et al. | 417/477.11 |
| 2008/0097320 A1 | 4/2008 | Moore et al. | |
| 2008/0114312 A1 * | 5/2008 | Muri et al. | 604/294 |
| 2011/0300010 A1 * | 12/2011 | Jarnagin et al. | 417/477.2 |

* cited by examiner

US 8,757,991 B2

PERISTALTIC PUMP AND INSERTABLE IRRIGATION LINE WITH A TUBE PORTION HAVING A DETERMINED PROFILE

This is a National Phase Application in the United States of International Patent Application PCT/EP2009/058120 filed Jun. 29, 2009, which claims priority on European Patent Application No. 08159641.3 of Jul. 3, 2008. The entire disclosures of the above patent applications are hereby incorporated by reference.

FIELD OF THE INVENTION

The present invention concerns a peristaltic pump and an irrigation line. More specifically, the present invention concerns a peristaltic pump for medical use intended to cooperate with an irrigation line connected to a physiological saline solution pouch.

BACKGROUND OF THE INVENTION

In the field of surgical procedures in the oral cavity and particularly in dental implantology, drilling and tapping has to be performed in the jaw bone. For this work to be carried out in good conditions, physiological saline solution has to be brought into the operating field area. The practitioner therefore has physiological saline solution pouches, which are emptied via a sterile irrigation line. This irrigation line is conventionally placed underneath the rollers of a peristaltic pump that continuously irrigates the operating field at a constant volume. When a physiological saline solution pouch is empty or between two successive patients, the practitioner has to remove the irrigation line and discard it with the saline solution pouch and then repeat the operation of fitting an irrigation line connected to a full saline solution pouch.

It has been observed that, with commercially available peristaltic pumps, placing the irrigation line underneath the pump rollers is not an easy operation. The practitioner has to use both hands in order to bend the irrigation line and shape it such that it can be put underneath the pump rollers. This is a difficult operation which requires dexterity on the part of the practitioner and which constitutes an addition to his work load. Further, it is not unusual for the practitioner to be unable to put the irrigation line in at the first attempt, so that he is obliged to repeat these operations.

The basic operating principle of a peristaltic pump is simple. When a roller compresses the irrigation line, it causes a volume of fluid to move forward and at the same time creates a depression that allows the inflow of the next volume of fluid. There are three rollers. It is clear that when the rollers rotate and successively compress the irrigation line, they exert a traction force thereon that is tangent to the circular trajectory of the rollers and oriented in the same direction as the rotational direction of the rollers. It is therefore necessary to provide means for immobilising the irrigation line next to the peristaltic pump rollers. Usually in commercially available peristaltic pumps, the irrigation line is clamped between two jaws upstream and downstream of the pump rollers. The drawback of this solution is immediately apparent: if the irrigation line is not suitably arranged and the jaws close on it, the irrigation line will be subject to shearing force and will be pierced.

It is an object of the present invention to overcome the aforementioned problems, in addition to others, by providing a peristaltic pump for surgical or dental use and an irrigation line, the implementation of which is extremely simple, requiring simple movements on the part of the practitioner and avoiding any risk of piercing or cutting the irrigation line.

SUMMARY OF THE INVENTION

The present invention thus concerns a flexible tube portion of an irrigation line according to a first embodiment or a second embodiment of this Patent Application. More specifically, in accordance with the first embodiment of the invention, a flexible tube portion for an irrigation line (1) connected to a supply of fluid for surgical or dental use is provided, wherein the flexible tube portion (4) is intended to cooperate with the rollers (62) of a peristaltic pump (16) for distributing the fluid, characterized in that it includes means (10A, 12A) that cooperate with complementary means (74A, 76A) of the pump (16) to define a distance between the two ends of the tube portion (4), which, combined with the length of the tube portion (4), gives the tube portion a determined profile enabling it to be positioned directly underneath the raceway of the rollers (62) of the pump (16). In accordance with a second embodiment of the present invention, a flexible tube portion for an irrigation line (1) connected to a supply of fluid for surgical or dental use is provided, wherein the flexible tube portion (4) is intended to cooperate with the rollers (62) of a peristaltic pump (16) for distributing the fluid, wherein it includes means (8, 10f, 12f) that define between the two free ends thereof a distance, which, combined with the length of the tube portion, gives the tube portion a determined profile enabling it to be positioned directly underneath the raceway of the rollers (62) of the pump (16).

The invention also concerns a peristaltic pump according to a ninth embodiment of this Patent Application. In particular, in accordance with the ninth embodiment, a peristaltic pump includes a plurality of rollers (62), which roll over a portion of flexible tube (4) of an irrigation line (1) connected to a supply of fluid for surgical or dental use, wherein it includes means (20) for receiving the flexible tube portion (4) in front of the plane in which the rollers (62) move, then for bringing the flexible tube portion (4) underneath the rollers (62) and then finally for pressing the portion against the rollers (62).

Advantageous embodiments of the flexible tube portion of the irrigation line and of the peristaltic pump, according to the invention, form the subject of additional embodiments. For example, in accordance with a third embodiment of the present invention, the second embodiment is modified so that it is assembled on a support part (8) provided with two tips (10f, 12f) on which the free ends of the tube portion are engaged. In accordance with a fourth embodiment of the present invention, the third embodiment is further modified so that the length of the flexible tube portion (4) and the distance separating the two tips (10f and 12f) are calculated such that the flexible tube portion (4) spontaneously adopts a shape enabling the tube portion to slide under the rollers (62) of the peristaltic pump (16). In accordance with a fifth embodiment of the present invention, the third and fourth embodiments are further modified so that the support part (8) includes means (10h, 12h, 64) for holding the part on the frame (18) of the pump (16). In accordance with a sixth embodiment of the present invention, the fifth embodiment is modified so that the support part (8) is flexible. In accordance with a seventh embodiment of the present invention, the sixth embodiment is further modified so that the support part (8) is provided with a gripping clamp (14) including two jaws (14a, 14b), which have to be pressed in order to bend the support part (8). In accordance with an eighth embodiment of the present invention, the third embodiment, the fourth embodiment, the fifth embodiment, the sixth embodiment and the seventh embodiment, are further modified so that the support plate (8) includes means (10: 10c, 10d, 10e, 10f, 10g; and 12: 12c, 12d, 12e, 12f, 12g) for connecting the flexible tube portion (4) both to an inlet tube (2) through which the fluid arrives and to an outlet tube (6) through which the fluid is expelled by the pump (16).

In accordance with a tenth embodiment of the present invention, the ninth embodiment is modified so that it includes a slide (20), which defines a housing (23) for receiving the flexible tube portion (4) and whose movements are controlled by a handle (22). In accordance with an eleventh embodiment of the present invention, the tenth embodiment is further modified so that the slide (20) and the handle (22) are both pivotally mounted about a common shaft (40) integral with the frame (18) of the pump (16). In accordance with a twelfth embodiment of the present invention, the eleventh embodiment is further modified so that the slide (20) and the handle (22) form a removable assembly together with the frame (18) of the pump (16) to which the slide and handle are secured. In accordance with a thirteenth embodiment of the present invention, the eleventh embodiment and the twelfth embodiment are further modified so that the peristaltic pump further includes a large surface (38) of the frame (18) parallel to the plane in which the rollers (62) move, characterized in that, during the movement that closes the slide (20), the handle (22) and the slide (20) are first of all pivotally coupled and both pivot about the common shaft (40) thereof (40) until the slide (20) abuts, via the tip thereof, against the large surface (38) of the frame (18) of the pump (16), wherein the base (68) of the slide (20) is at a distance from the large surface (38) of the frame (18), and the handle (22) then is uncoupled from the slide (20) and continues to pivot about the shaft (40) thereof, forcing the slide (20) to make a composite swivelling motion that tends to return the base (68) against the large surface (38) of the frame (18) of the pump (16) and a vertical translation motion upwards into a position in which the slide extends parallel to the large surface (38) of the frame (18) of the pump (16).

In accordance with a fourteenth embodiment of the present invention, the thirteenth embodiment is further modified so that a stud (52) integral with the slide (20) follows a cam path (50) provided on the handle (22) and in that the common pivot shaft (40) of the slide (20) and the handle (22) projects into a cam path (44) provided on the slide (20), wherein the cam path (44) moves relative to the common pivot shaft (40). In accordance with a fifteenth embodiment of the present invention, the thirteenth embodiment and the fourteenth embodiment are further modified so that the handle (22) is provided with at least one arm (54) that cooperates with a cam profile (58) provided on the slide (20) for temporarily pivotally coupling the slide (20) and the handle (22), wherein the arm (54) moves, via the free end (56) thereof, into a notch (60) provided on the frame (18) of the pump (16), when the assembly formed by the slide (20) and the handle (22) is in the closed position. In accordance with a sixteenth embodiment of the present invention, the fifteenth embodiment is further modified so that the handle (22) has a shoulder (17), which, when the handle (22) is in the closed position, moves under a plane surface (58b) of the cam path (58). In accordance with a seventeenth embodiment of the present invention, the thirteenth embodiment, the fourteenth embodiment, the fifteenth embodiment, and the sixteenth embodiment, are further modified so that the slide (20) includes at least one catch (28), partially separated from the slide (20) by a vertical groove (32) and ending in a tooth (34), the function of which is to limit the clearance of the slide (20), when the slide is opened or closed, the catch (28) sliding into a vertical slot (36) arranged in the large surface (38) of the frame (18) of the pump (16), the large face (38) of the frame (18) projecting into the groove (32) when the slide (20) is in the closed position.

Owing to these features, the present invention provides a portion of flexible tube of an irrigation line which, because of its length and the distance that separates its two ends, has a profile enabling it to be positioned directly on the raceway of peristaltic pump rollers, without the practitioner having to bend the tubing or handle it in any other way in order to fix it to the pump. The practitioner therefore saves time and avoids any unnecessary stress, which could adversely affect the course of his procedure. Further, the risk of ruining the irrigation line for example by piercing it, or damaging the pump are practically non-existent.

The movement required to assemble the flexible tube portion is also simplified as far as possible. Indeed, the means carrying the flexible tube portion only need to be slightly bent in order to assemble the tube portion to the pump. This operation is carried out using two fingers of the same hand.

The peristaltic pump according to the invention includes means for receiving the flexible tube portion in front of the plane in which the rollers move, which, as will easily be understood, considerably simplifies the operation of connecting the flexible tube portion, given that the presence of the rollers is not a hindrance. Then, with a simple movement by the practitioner, the tube portion is moved underneath the raceway of the rollers and finally pressed against the rollers, and is thereby placed in the working position. By automating the operation of fitting the tube portion, the practitioner is relieved of a task, which, in the past, could be long and tedious and which involved a non negligible risk of piercing the tube or damaging the pump if the tube was poorly positioned.

BRIEF DESCRIPTION OF THE DRAWINGS

Other features and advantages of the present invention will appear more clearly from the following detailed description of one embodiment of the irrigation line and peristaltic pump according to the invention, this example being given solely by way of non-limiting illustration with reference to the annexed drawing, in which.

DETAILED DESCRIPTION OF THE ILLUSTRATIVE EMBODIMENTS

The invention concerns both a peristaltic pump and an irrigation line for conveying physiological saline solution into the operating field. We will first consider the irrigation line, and the peristaltic pump will be described secondly.

Figure 1:
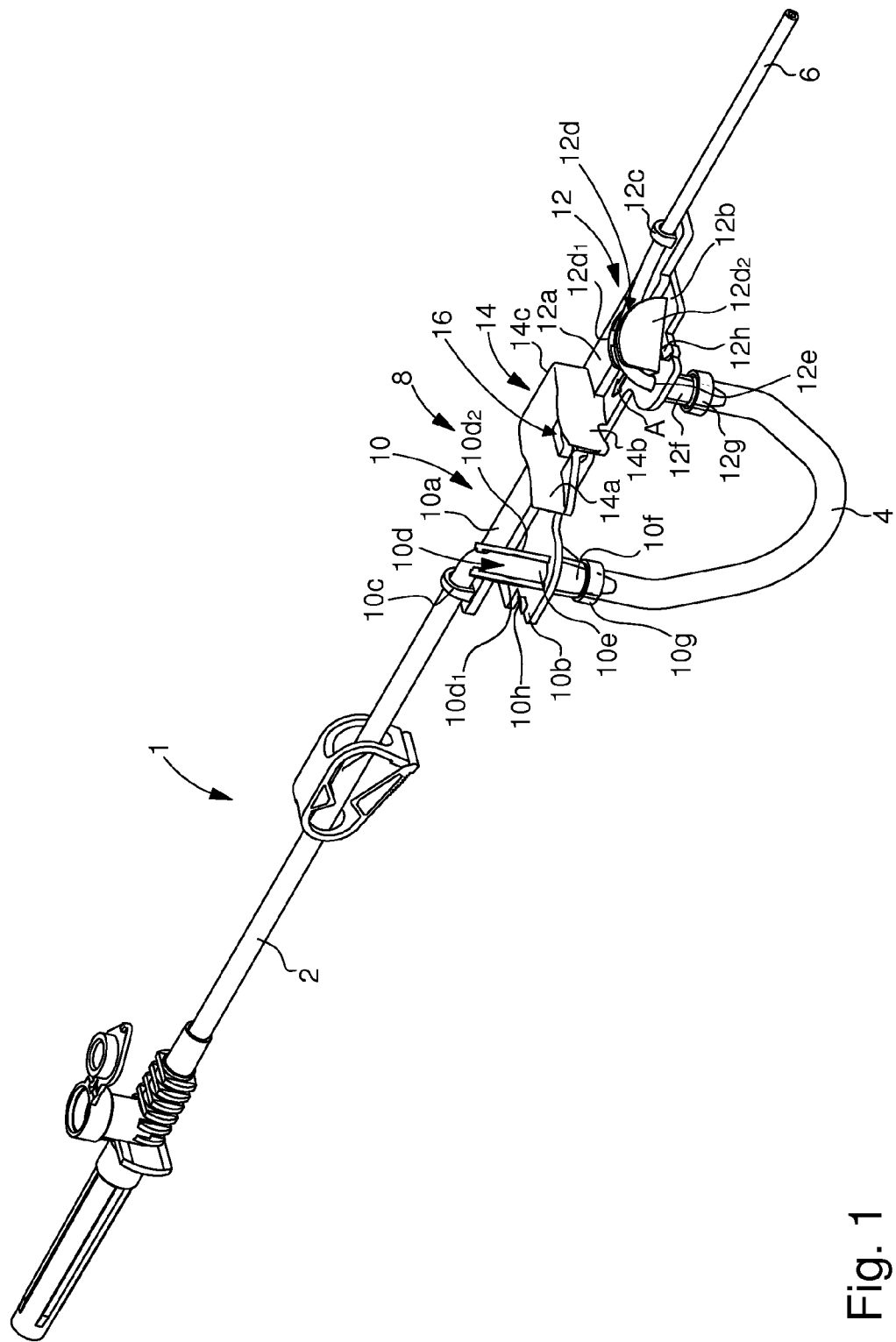
FIG. 1 is a perspective view of the irrigation line in accordance with an embodiment of the present invention.

The irrigation line, designated as a whole by the general reference number 1, includes (see FIG. 1) three portions of tubing, namely an inlet tube 2 which is connected to a physiological saline solution pouch (not shown) and which is extended in succession by a pump tube 4 and an outlet tube 6. Inlet tube 2 and outlet tube 6 are typically made of PVC. Pump tube 4 is preferably made of silicon, but it may also be made of PVC or another flexible and resistant material.

The peristaltic pump rollers, which will be described in detail below, roll over pump tube 4. When, at a given time, one of the rollers crushes pump tube 4, it causes a volume of fluid to move towards outlet tube 6 and at the same time creates a depression which allows the inflow of another volume of fluid from the pouch via inlet tube 2.

Pump tube 4 is preceded by inlet tube 2 and followed by outlet tube 6.

Irrigation line 1 according to the invention is completed by a support part 8. This support part 8 is of generally rectilinear shape and has two stepped arms 10 and 12 which are resiliently connected to each other by a U-shaped gripping clamp 14 provided with two jaws 14a and 14b. The two jaws 14a, 14b of the gripping clamp 14 are connected to each other by a bottom wall 14c, which also connects the two stepped arms 10 and 12. It will be noted that the resilience of the two stepped arms 10 and 12 is obtained by removing matter visible at 16 between the two jaws 14a, 14b of gripping clamp 14.

Each of the two stepped arms 10 and 12 has the same structure formed by a base plate 10a, 12a which extends in front of and at a lower level than a side bar 10b, 12b. Thus, at the free end of side bar 10b of stepped arm 10 there is a ring 10c under which inlet tube 2 is placed. Inlet tube 2 then goes into a guide groove 10d in the arc of a circle delimited by two vertical walls $10d_1$ and $10d_2$, before penetrating a hole 10e in which it can be bonded by means of a sterilisable biocompatible adhesive or secured by any other method, such as, for example, ultrasonic welding. Hole 10e opens out under the bottom surface of base plate 10a in a notched tip 10f onto which one of the ends of pump tube 4 is forced, then crimped by means of a crimping ring 10g which can be moved manually so that it covers the end of pump tube 4.

In a similar manner, the other free end of pump tube 4 is forced onto a notched tip 12f and crimped by means of a crimping ring 12g. Notched tip 12f emerges onto the top face of base plate 12a in a hole 12e in which one of the free ends of outlet tube 6 is engaged and possibly bonded or even ultrasound welded. Outlet tube 6 then goes into a guide groove 12d in the arc of a circle delimited by two vertical walls $12d_1$ and $12d_2$ before being slid underneath a ring 12c which stands at the free end of side bar 12b.

At the end that remains free, inlet tube 2 is connected to a physiological fluid pouch (not shown). The free end of outlet tube 6 is connected to a dental or surgical instrument.

It will be appreciated henceforth that the length of pump tube 4 and the distance separating the two notched tips 10f and 12f are calculated such that the pump tube 4 spontaneously adopts a shape that makes it able to slide under the rollers of the peristaltic pump according to the invention.

The presence of a locking stud, respectively 10h, 12h, is also noted on each of base plates 10a, 12a of the two stepped arms 10 and 12. The locking studs are for locking support part 8 onto the frame of the peristaltic pump as described in detail below.

It will also be clear that, because of the resilience of support part 8, the two locking studs 10h, 12h tend to move closer together when the user grips jaws 14a, 14b of gripping clamp 14 between two of his fingers. Two arrows, referenced A in the drawing, also invite the user to exert pressure on jaws 14a, 14b of clamp 14.

It will be noted finally that the irrigation line is, of course, delivered completely assembled to the user. The user will thus only need to insert the pump tube part of the irrigation line into the frame of the peristaltic pump, then connect the line both to the physiological fluid pouch and to the surgical or dental instrument that he is to use.

We will now consider the peristaltic pump according to a second aspect of the invention.

Figure 2:
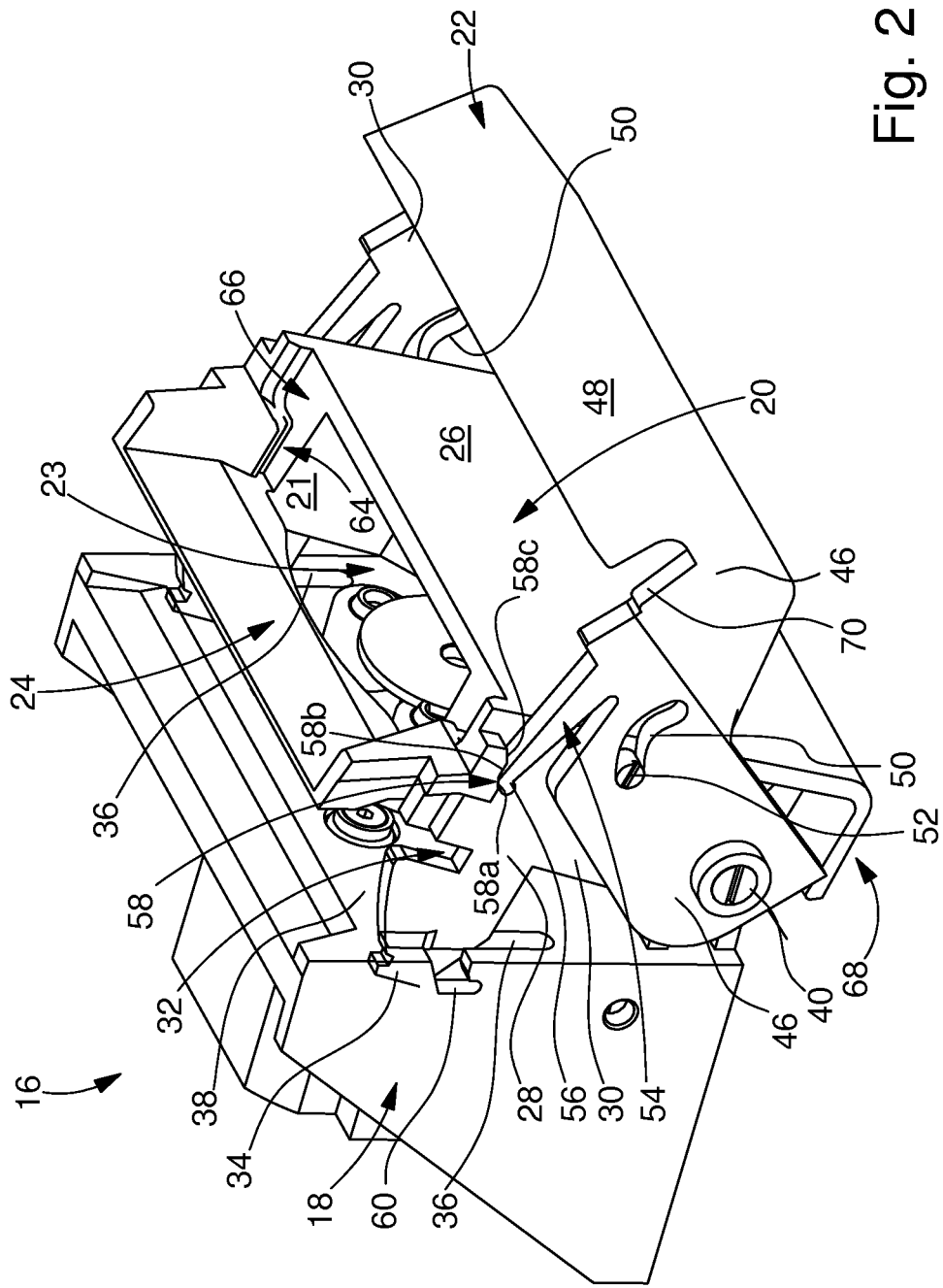
FIG. 2 is a perspective view of the empty slide in the open position, in accordance with the embodiment of FIG. 1.
Figure 3:
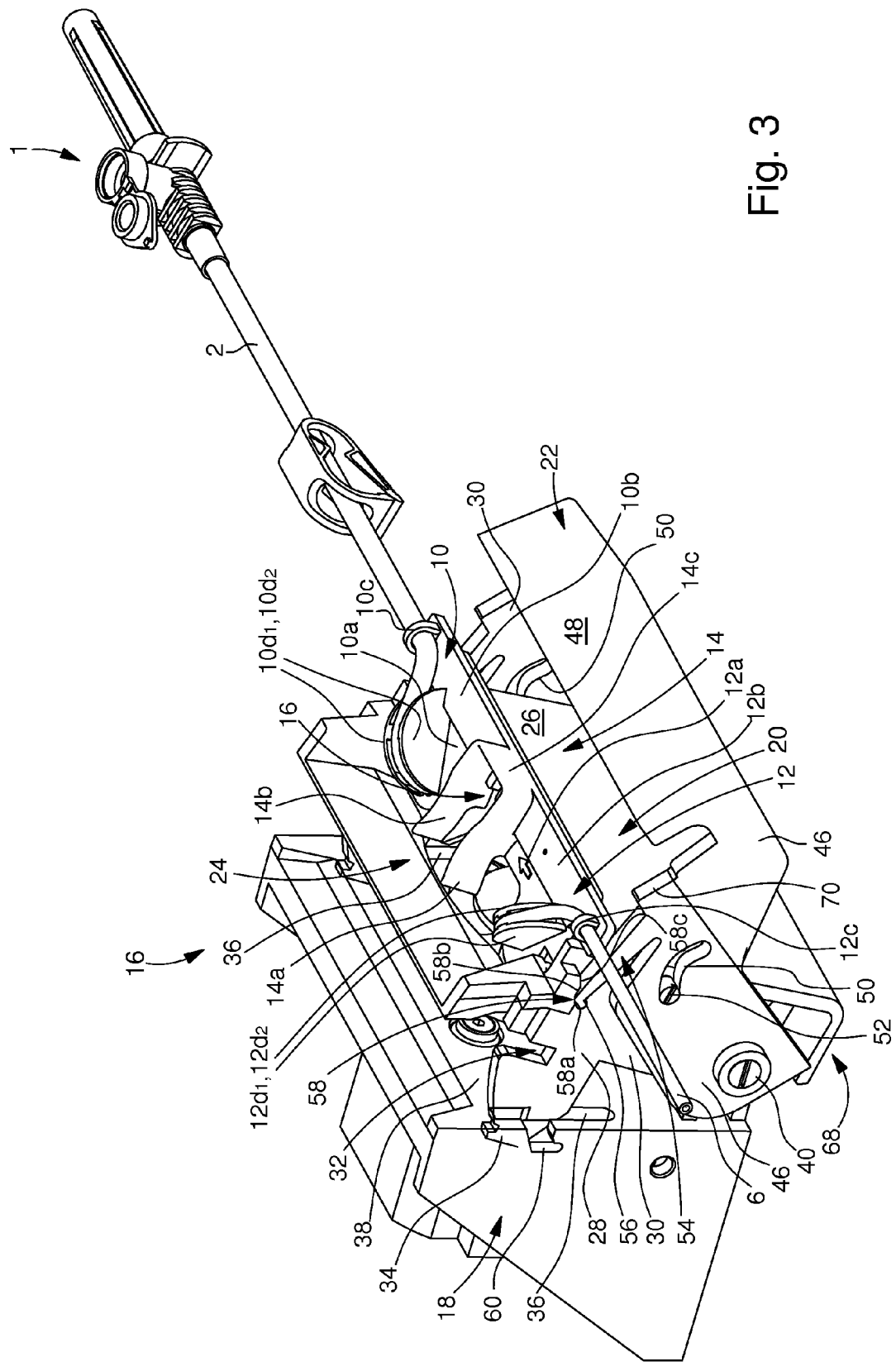
FIG. 3 is a perspective view of the slide in the open position with the irrigation line loaded in the slide, in accordance with the embodiment of FIG. 1.

Designated as a whole by the general reference numeral 16, the peristaltic pump according to the invention essentially includes (see FIG. 2) a frame 18, a slide 20 and a handle 22. FIG. 2 shows the peristaltic pump 16 with the empty slide 20 thereof in an open position. It will be noted immediately that slide 20 has a generally parallelepiped external shape and defines, with an inner wall 21 substantially in the arc of a circle, a housing 23 for receiving irrigation line 1 and more specifically support part 8 and pump tube 4. Slide 20 is extended upwards by a stop plate 24, which extends parallel to and set back from the front face 26 of slide 20. At least one and preferably two catches 28 are provided in the continuation of the small sides 30 of slide 20, at the top end of the small sides 30. It is noted that catches 28 each have a vertical groove 32 which partly separates them from the small sides 30 of slide 20 and that they end in a tooth 34, the function of which is to limit the clearance of the slide 20 when it is opened. Indeed, as will be seen below, slide 20 essentially makes a pivoting movement during which catches 28 slide into two vertical slots 36 arranged in the large surface 38 of frame 18, such that, when slide 20 is completely open, it is retained by teeth 34 of catches 28 which then engage with the large surface 38 of frame 18.

Slide 20 and handle 22 are pivotally mounted on frame 18 of pump 16 about two common pivot pins or shafts 40 located on either side of the unit formed by slide 20 and handle 22. It is noted that slide 20, handle 22 and frame 18 of pump 16 onto which slide 20 and handle 22 are mounted, form an independent and removable constructive assembly. Thus, if the motor of pump 16 breaks down, for example, a standard exchange can simply be made between the defective assembly and a new assembly. Likewise, the removable constructive assembly according to the invention can either be placed in a case provided especially for this purpose, or, for example, in a power and control unit, commonly known as a "unit" that all practitioners own.

Figure 4A:
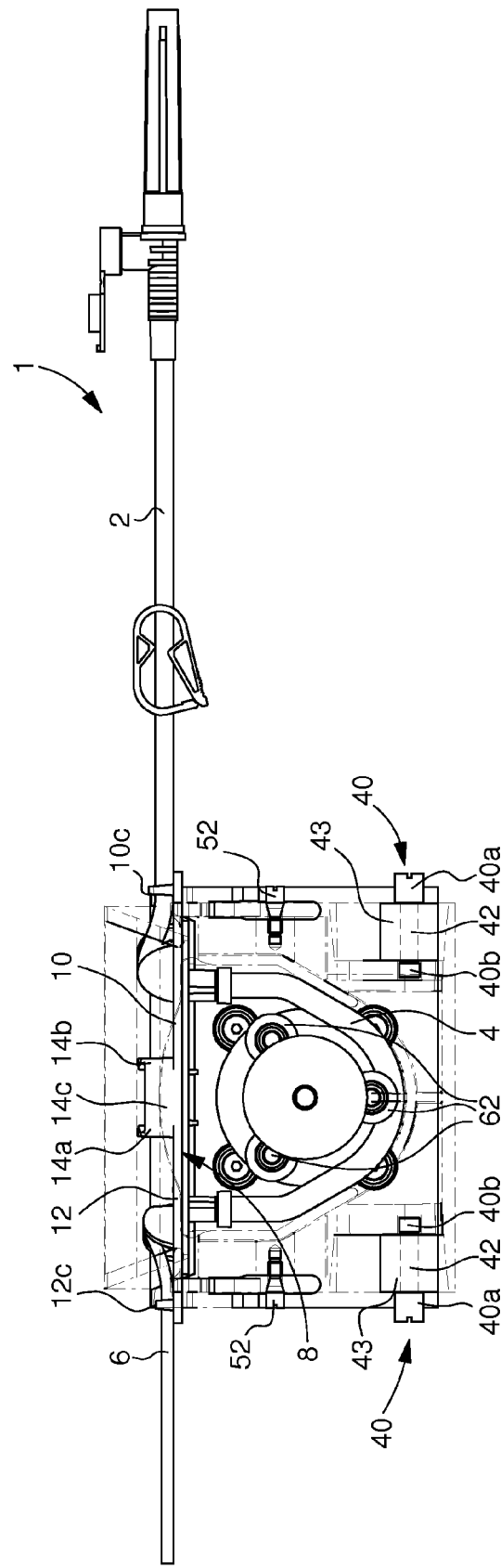
FIG. 4a is a front view of the peristaltic pump with the irrigation line of FIG. 1 in place and the slide omitted.
Figure 4B:
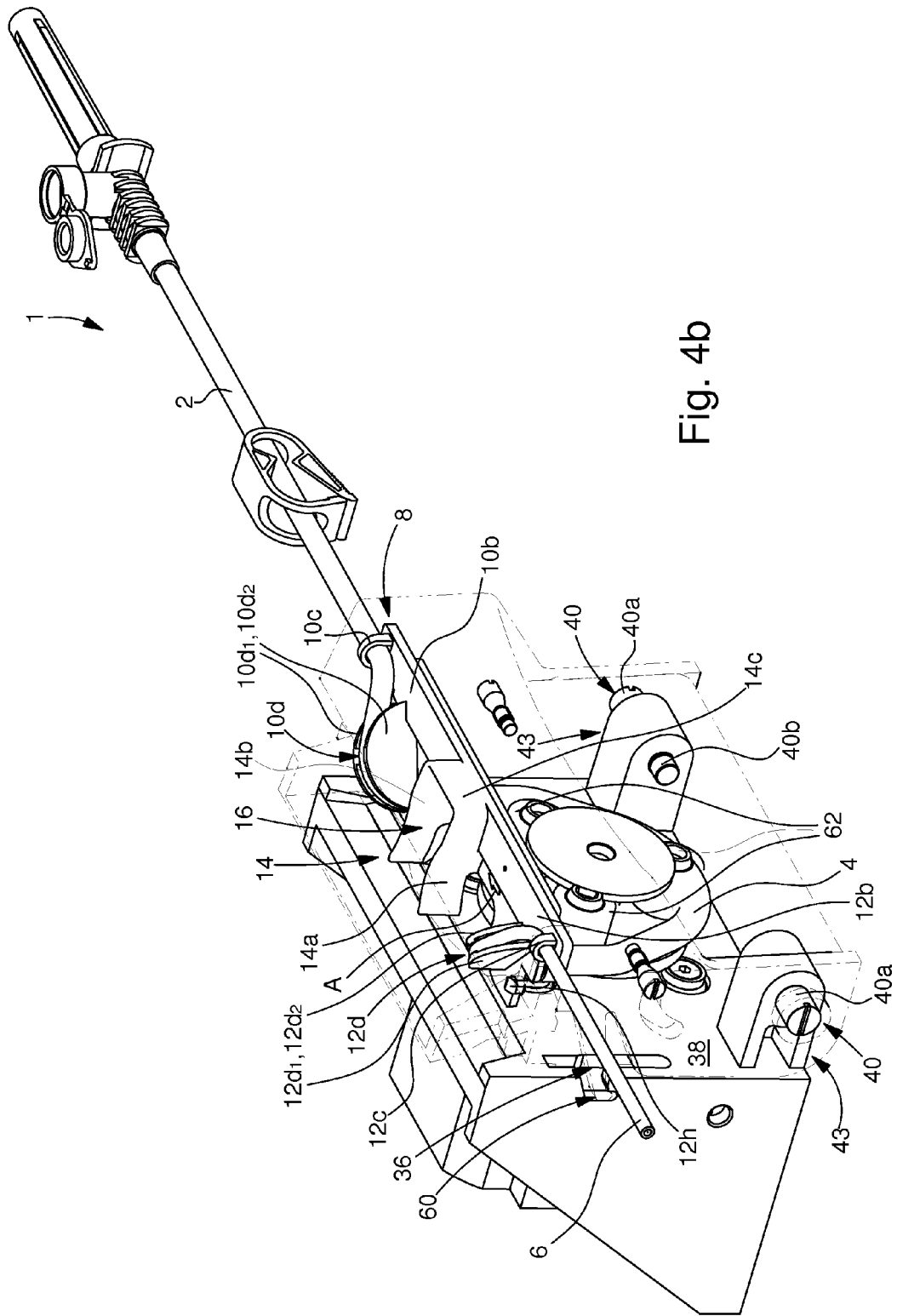
FIG. 4b is a perspective view of the peristaltic pump with the irrigation line of FIG. 1 in place and the slide omitted.

Each pivot shaft 40 emerges from both sides of a through hole 42 made in a rib 43 which extends perpendicularly to the large surface 38 of frame 18 (see FIGS. 4a and 4b). At the first free end 40a thereof, pivot shaft 40 serves as a support for slide 20 via handle 22. At the second free end 40b thereof, pivot shaft 40 follows the profile of a cam channel or path 44 arranged on the external face of the inner wall 21 of slide 20 (see FIGS. 5a and 5b).

Handle 22 is essentially formed of two vertical walls 46, which are parallel to each other and connected by an actuation bar 48. It is noted that each of walls 46 of handle 22 has a banana-shaped cam path 50 which is followed by a stud 52 secured by any suitable means in the small side 30 of slide 20.

It is noted finally that handle 22 has two inclined arms 54, which extend parallel to the small sides 30 of slide 20 and which each end in a stud 56. As will be seen below, these two inclined arms 54 cooperate alternately with a cam path 58 provided at the top end of the small side 30 of slide 20 and with a notch 60 arranged on the sides of the large face 38 of frame 18. It will be noted that cam path 58 has two parallel and inclined planes 58a and 58c connected to each other by a horizontal plane 58b.

We will now consider the operation of loading irrigation line 1 and closing slide 20. Movements that tend to move slide 20 and handle 22 away from frame 18 of pump 16 will be called positive movements, and movements that tend to move slide 20 and handle 22 closer to frame 18 of pump 16 will be called negative movements.

Figure 5A:
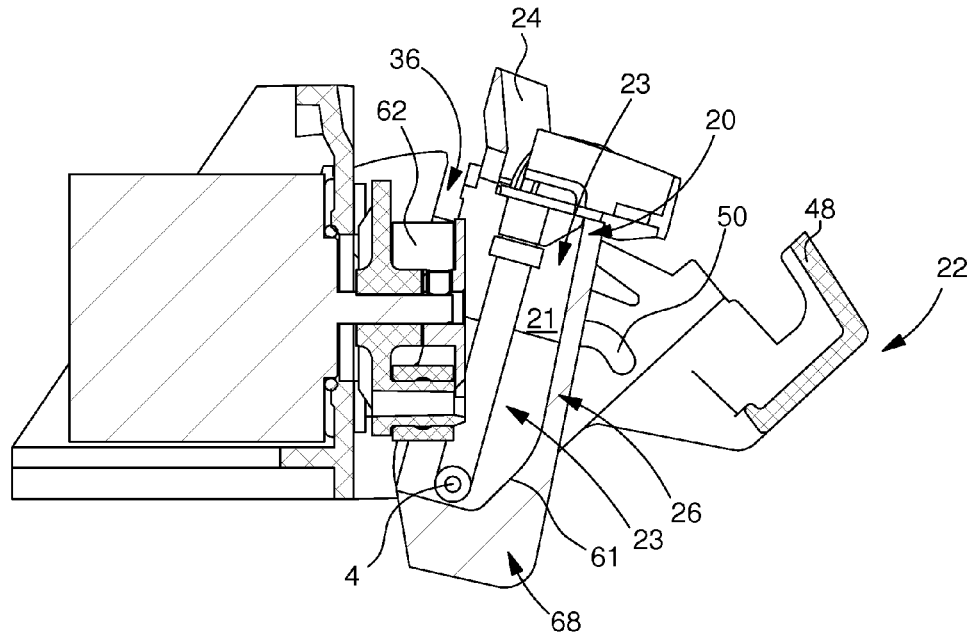
FIG. 5a is a side cross-sectional view of the slide with the slide completely open.

The operation of setting irrigation line 1 in place starts with the introduction of pump tube 4 and support part 8 into housing 23 of slide 20 (see FIG. 5a). The shape of inner wall 21 substantially follows the profile of pump tube 4. Pump tube 4 is pre-positioned in housing 23 by a guide cam 61 that is provided in the bottom of the housing 23 and orients pump tube 4 towards rollers 62 of peristaltic pump 16 (see FIG. 5a). Support part 8 is inserted into housing 23 with the open side of the two jaws 14a, 14b of clamp 14 facing towards rollers 62 of pump 16.

As already mentioned above, to allow support part 8 to be easily assembled in housing 23 of the slide, the user only has to squeeze the two jaws 14a, 14b of clamp 14 with two of his fingers. Because of their resilience, the two stepped arms 10, 12 will bend and locking studs 10h, 12h will move closer to each other, which will allow to present them face a groove 64 arranged at the base of stop plate 24 (see FIG. 2). When the user releases the pressure on the two jaws 14a, 14b of clamp 14, locking studs 10h, 12h will project into groove 64, via their inclined face, thus ensuring that support part 8 is held in slide 20.

Thus engaged, support part 8 rests on the edge 66 of slide 20 (see FIG. 2) via base plates 10a, 12a of the arms 10 and 12 thereof. The user therefore only needs to slide pump tube part 4 of irrigation line 1 into housing 23 of slide 20 and exert slight pressure on jaws 14a, 14b of clamp 14 to position support part 8 in the slide 20. This is an extremely simple and almost intuitive operation, which requires the use of only one hand. Moreover, the user does not need to adjust the profile of pump tube 4 at any time so that the latter adapts to the profile of the raceway of rollers 62 of pump 16 according to the invention. The user thus saves precious time, avoids any unnecessary stress and is not liable to damage the irrigation line, or the pump itself because of poor positioning of the pump tube relative to the pump rollers.

Figure 5B:
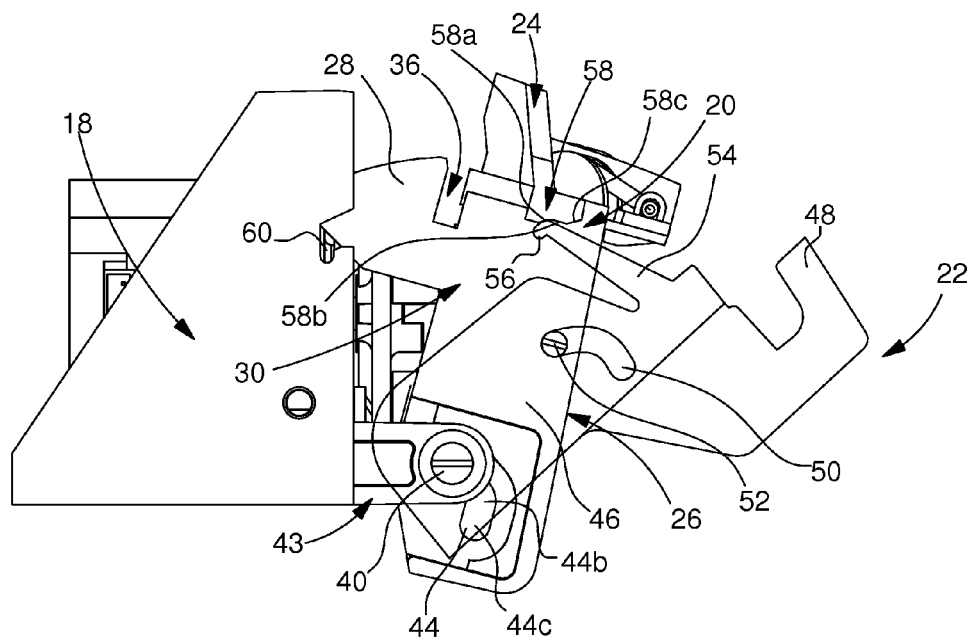
FIG. 5b is a side view of the pump with the slide completely open.

When pump tube 4 and the support part 8 thereof are in position in housing 23 of slide 20, the slide can start to be closed (see FIGS. 5a and 5b). Thus a thrust is exerted on actuation bar 48 of handle 22 in the negative direction, i.e. in the direction of frame 18 of pump 16. Handle 22 then starts to pivot about pivot shaft 40, driving with it slide 20 in the same swivelling motion about the shaft 40. In fact, at this stage of the movement, slide 20 and handle 22 are coupled via the two inclined arms 54 of handle 22 which abut, via the studs 56 thereof, against the inclined planes 58a of cam paths 58. The slide is also prevented from moving upwards by catches 28 sliding in grooves 36.

Figure 7A:
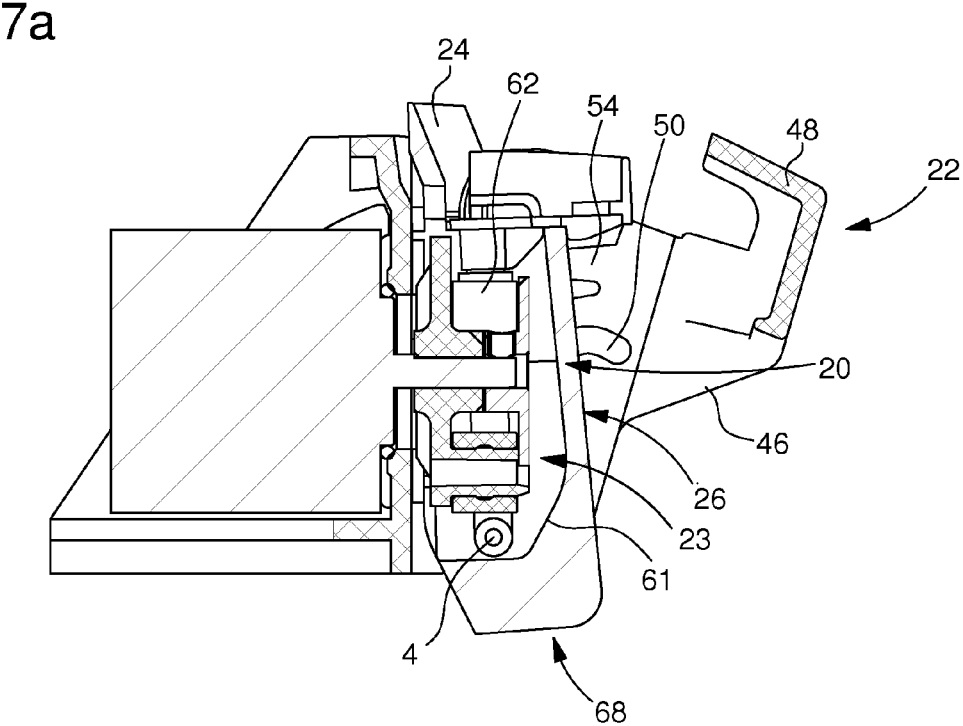
FIG. 7a is a side cross-sectional view of the pump with the slide in a second intermediate position.
Figure 7B:
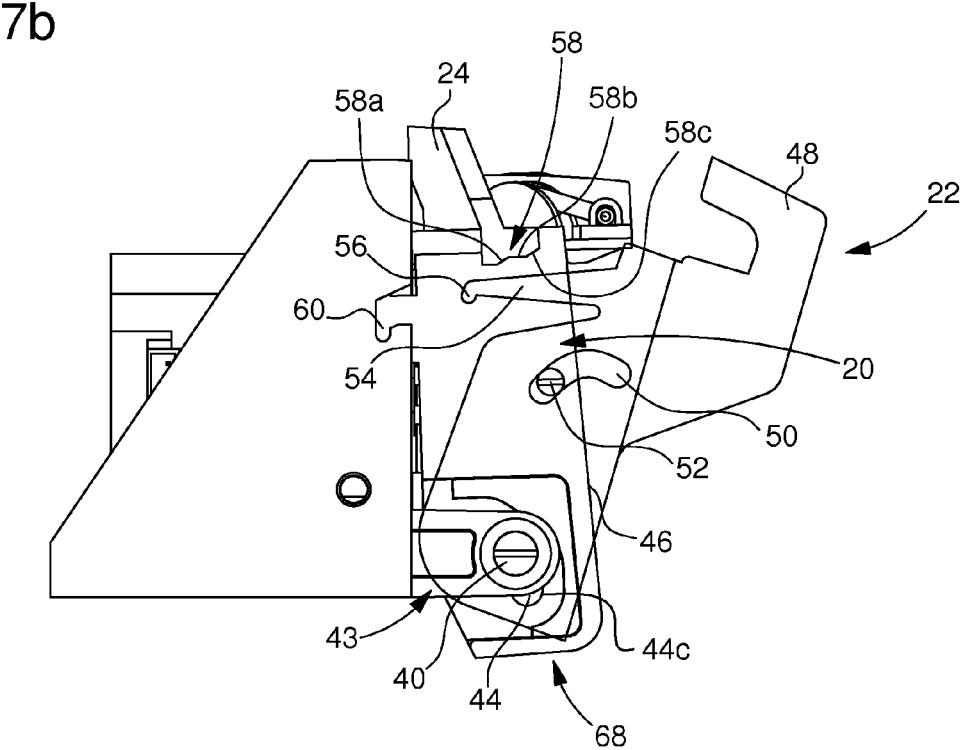
FIG. 7b is a side view of the pump with the slide in a second intermediate position.

Handle 22 thus causes slide 20 to swivel in the negative direction about shaft 40 towards frame 18 of pump 16 until stop plate 24 of slide 20 abuts against the top part of the frame 18. At that moment (see FIGS. 7a and 7b), studs 56 of inclined arms 54 slip out of inclined planes 58c of cam paths 58, and handle 22 and slide 20 are no longer pivotally coupled to each other.

Figure 6A:
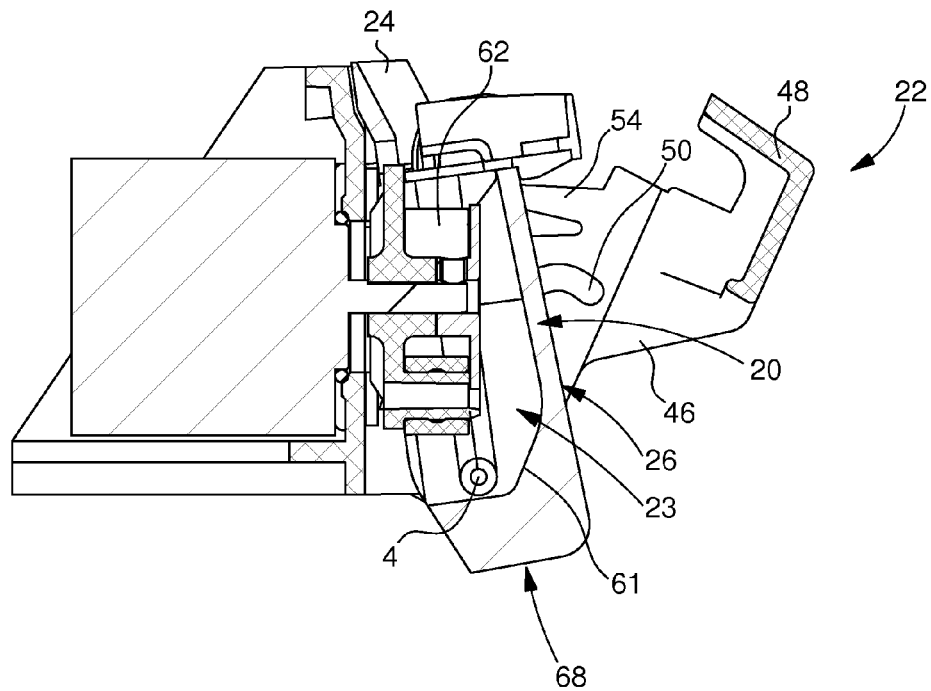
FIG. 6a is a side cross-sectional view of the slide with the slide in a first intermediate position.
Figure 6B:
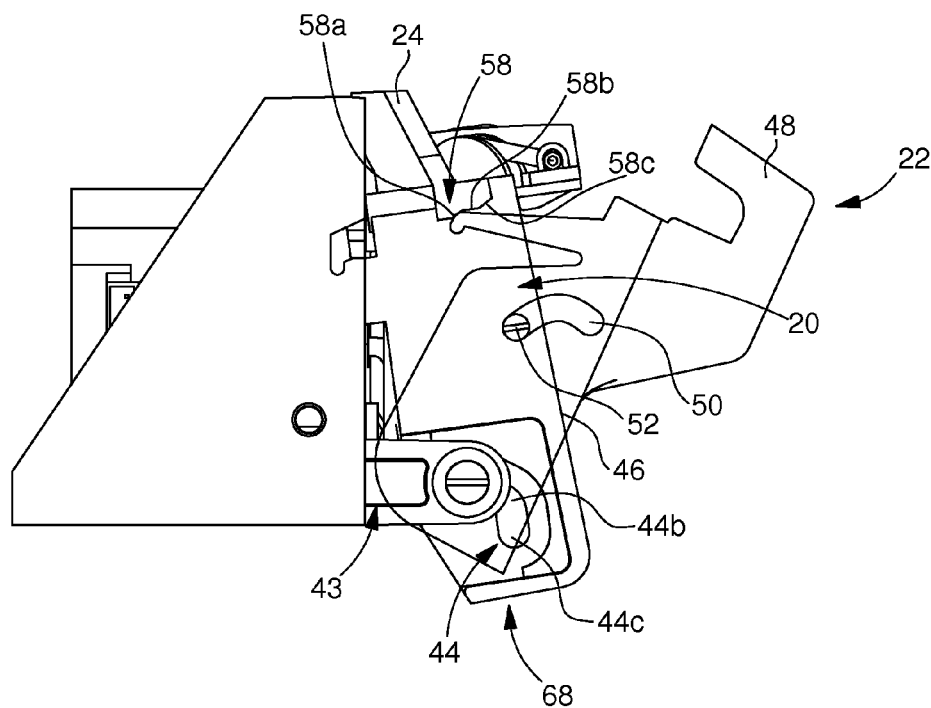
FIG. 6b is a side view of the pump with the slide in a first intermediate position.

When handle 22 continues to be pushed towards frame 18 of pump 16 via action on actuation bar 48, the handle 22 continues its swivelling movement about shaft 40, whereas slide 20 makes a combined swivelling and upwards translation motion. It is noted (see FIGS. 6a and 6b) that at the moment when handle 22 and slide 20 are uncoupled, slide 20 is in an inclined position with its base 68, which is spaced apart from frame 18 of pump 16. It should be understood that base 68 of slide 20 is at substantially the same level as pump tube 4 at the bottom of housing 23. Consequently, in this position, where slide 20 is inclined, pump tube 4 is still clear of the raceway of rollers 62 of pump 16, which makes it easier to close slide 20.

Figure 8:
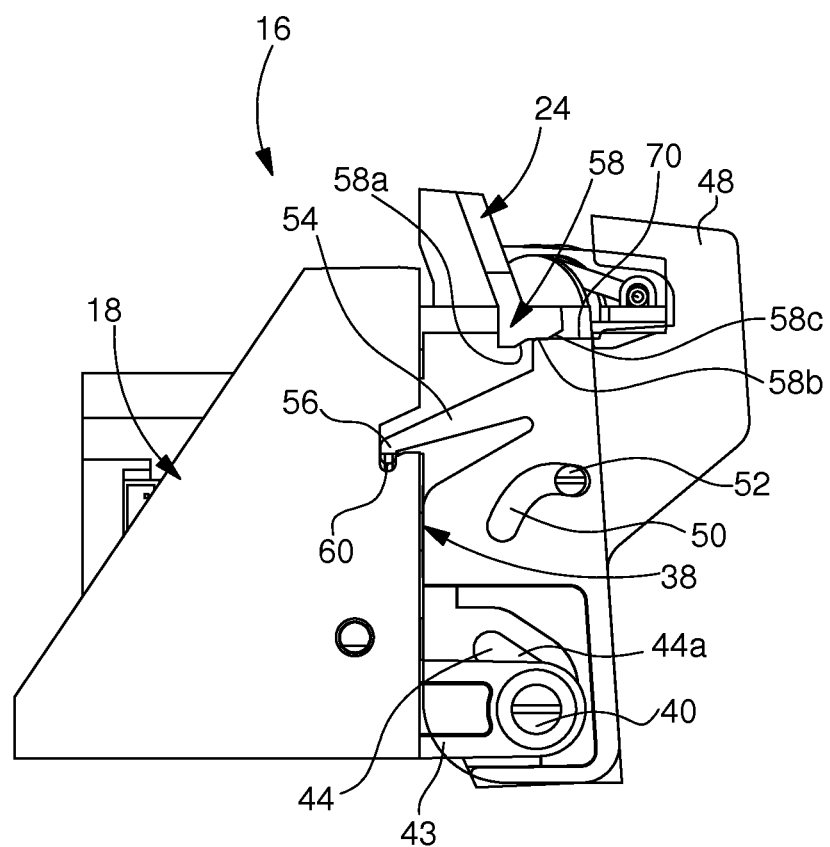
FIG. 8 is a side view of the pump with the slide closed.

However, pump tube 4 must then be able to be moved under the raceway of rollers 62, and then forced against the rollers 62. This is achieved as a result of the dual swivelling and upwards translation motion of slide 20. In fact, during the swivelling motion of handle 22, slide 20 also swivels and is guided in its motion by cam path 44 which moves relative to the second free end 40b of pivot shaft 40. This cam path 44 has two rectilinear portions 44a and 44c connected to each other by a bent portion 44b. At the start of the swivelling motion of slide 20 (FIG. 5a), pivot shaft 40 is at the bottom of the first rectilinear portion 44a of cam path 44. At the end of the swivelling motion of slide 20 (FIG. 8), pivot shaft 40 is at the bottom of second rectilinear portion 44c of the cam path 44. This relative motion of cam path 44 with respect to pivot shaft 40 of slide 20 returns slide base 68 to a position abutting against frame 18 of pump 16. Simultaneously, stud 52 fixed to slide 20 moves from the bottom upwards in cam path 50 arranged in handle 22. This motion ends the phase of closing slide 20 by forcing slide 20 to perform a vertical translation motion from the bottom upwards. Thus, by returning base 68 of slide 20 to a position abutting against frame 18 of pump 16 during the first rising phase of slide 20, pump tube 4 is brought underneath the raceway of rollers 62 while the vertical translation motion upwards of slide 20 forces the pump tube 4 against the rollers 62.

Slide 20 is finally locked (see FIG. 8) by studs 56 of inclined arms 54 which move into notches 60 arranged on frame 18 of pump 16, so as to prevent slide 20 from opening under the effect of vibrations caused by rollers 62. It is also seen that handle 22 has a shoulder 70, which, when handle 22 is in the closed position, moves under the flat surface 58b of cam path 58 so as to hold slide 20 in the high position and to withstand the radial stress of rollers 62. Finally the large surface 38 of frame 18 projects into vertical grooves 32 of catches 28 to ensure that slide 20 and handle 22 are pivotally locked.

Figure 9:
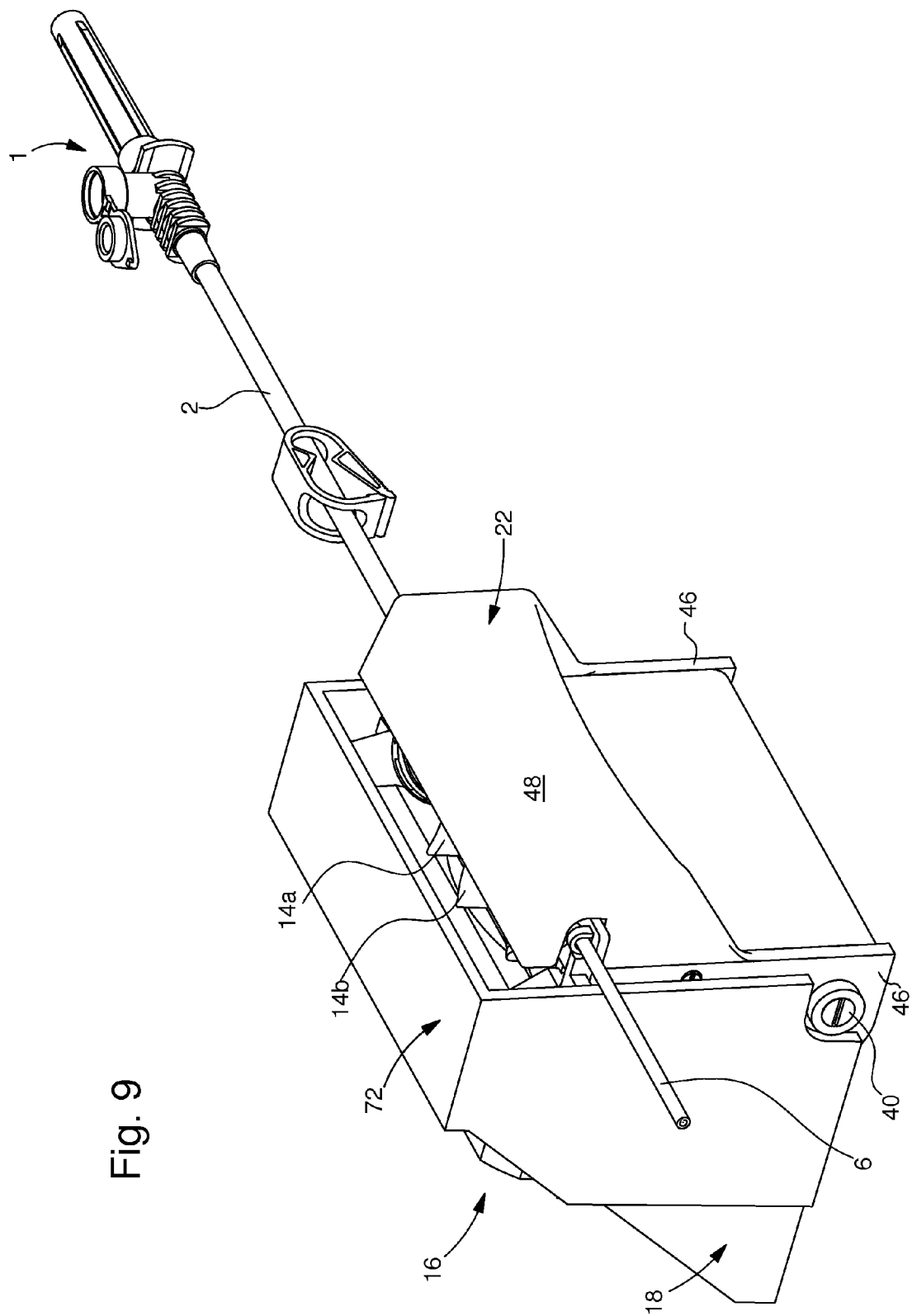
FIG. 9 is a perspective view of the slide in the closed position.

The pump is shown in the closed position in FIG. 9, with a cap 72 covering the assembly.

Slide 20 is unlocked by performing, in reverse order, the steps described above for closing slide 20. First of all, traction is exerted on actuation bar 48 of handle 22 in the positive direction. Handle 22 then starts to pivot about its shaft 40, which causes studs 56 to leave notches 60 and the withdrawal of shoulder 70 under flat surface 58b of cam path 58. Simultaneously, stud 52 secured to slide 20 moves from the top down in cam path 50, arranged in handle 20, which forces slide 20 to perform a vertical movement of translation from the top down. This movement moves pump tube 4 away from the raceway of rollers 62 by firstly lowering pump tube 4 relative to the level of rollers 62. In parallel, cam path 44 moves relative to the second free end 40*b* of pivot shaft 40. At the start of the swivelling motion of slide 20, pivot shaft 40 is at the bottom of the second rectilinear portion 44*c* of cam path 44. At the end of the swivelling motion of slide 20, pivot shaft 40 is at the bottom of the first rectilinear portion 44*a* of the cam path 44. This relative motion of cam path 44 with respect to pivot shaft 40 of slide 20 causes base 68 of slide 20 to pivot in the positive direction moving it away from frame 18 of pump 16 and thus moving pump tube 4 away from the raceway of rollers 62.

When it reaches a certain point in its swivelling motion, handle 22 is coupled with slide 20 via studs 56 of its inclined arms 54, which mesh with the inclined planes 58*c* of cam paths 58. Handle 22 thus causes slide 20 to swivel in the positive direction around pivot shaft 40 moving it further away from frame 18 of pump 16, as a result of which pump tube 4 and support part 8 are completely released from the frame 18. It will be noted that slide 20 stops swivelling when teeth 34 of catches 28 are meshed with the large surface 38 of frame 18. It will be noted that during the vertical downward motion of slide 20, vertical grooves 32 are released from the hold of large surface 38 of frame 18. Then, a simple application of pressure on jaws 14*a*, 14*b* or clamp 14 is enough to release the locking studs 10*h*, 12*h* from grooves 64 and to enable pump tube 4 and its support part 8 to be removed from slide 20.

Figure 10:
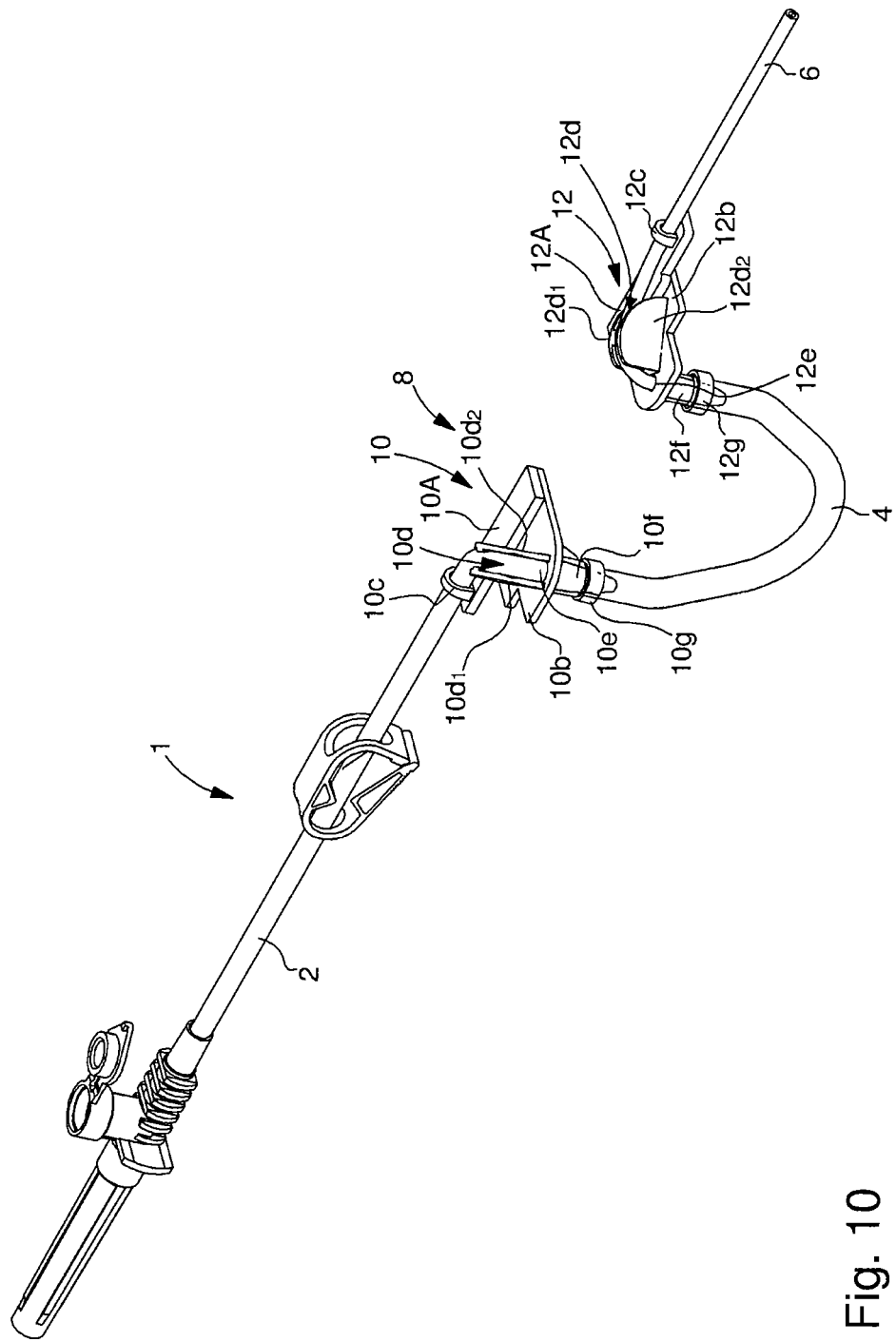
FIG. 10 is a perspective view of the irrigation line in accordance with another embodiment of the present invention.
Figure 11:
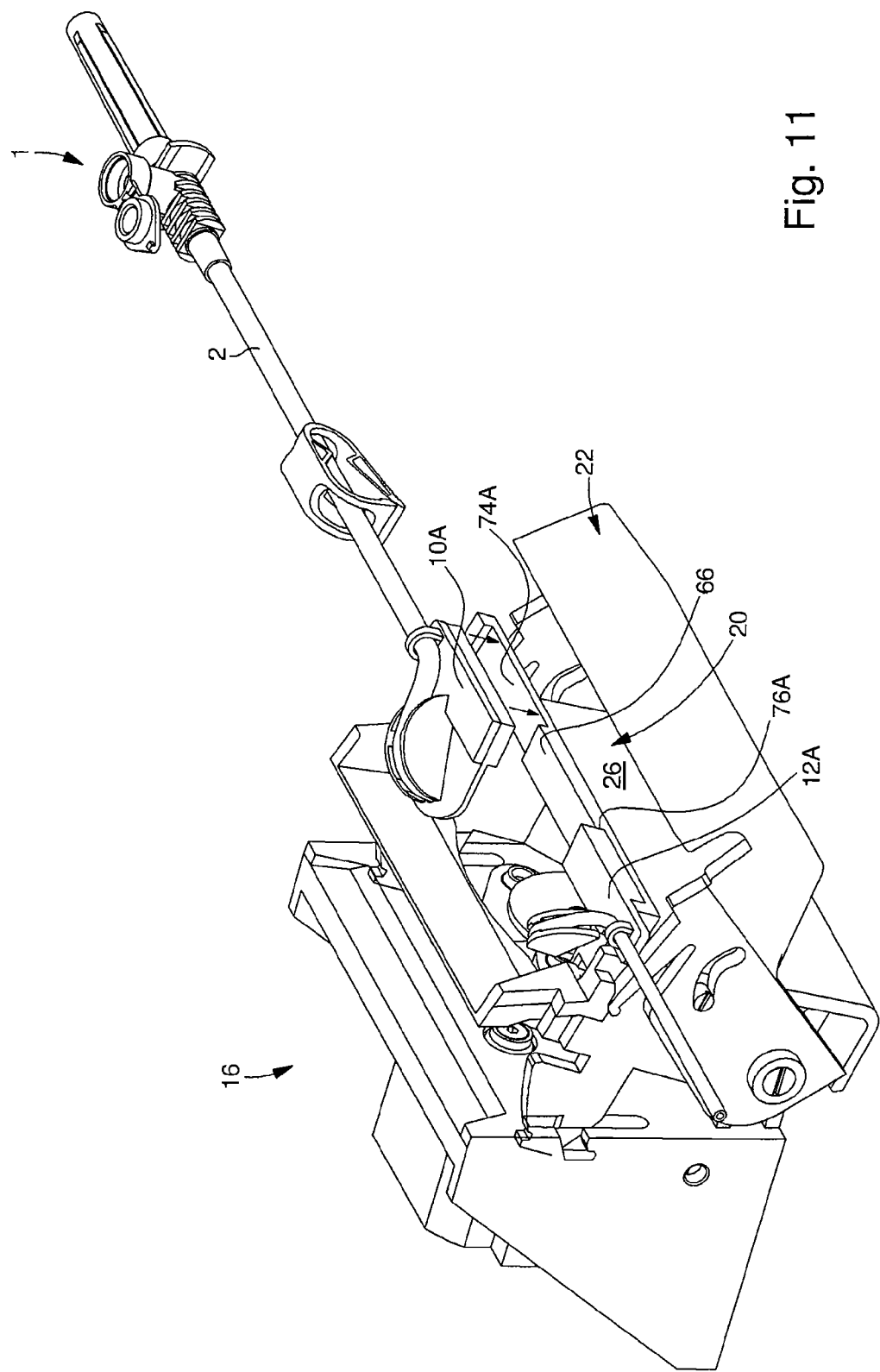
FIG. 11 is a perspective view of the slide in the open position with the irrigation line of FIG. 10 loaded in the slide.

According to an alternative embodiment of the invention as shown in FIGS. 10 and 11, the flexible tube portion 4 of a determined length may include means that cooperate with complementary means of pump 16 to define a distance between the two ends of tube portion 4 that gives the latter, in combination with the length of the tube portion 4, a determined profile allowing it to be positioned directly underneath the raceway of rollers 62 of pump 16. It is thus possible to envisage providing each of the ends of flexible tube portion 4 with a coupling part 10A, 12A in a similar shape to that of base plates 10*a*, 12*a*. These two coupling parts, 10A, 12A, which are not joined to each other, would each have a hole 10*e*, 12*e* for assembling inlet tube 2 and outlet tube 6 respectively. These holes 10*e*, 12*e* would open out into notched end portions 10*f*, 12*f* onto which the free ends of pump tube 4 would be forced and crimped. Moreover, two holes 74A, 76A could be provided, for example, in the edge 66 of slide 20, for receiving the coupling parts 10A, 12A that are similar in shape to base plates 10*a*, 12*a*.

The invention claimed is:
1. A peristaltic pump including:
(a) a plurality of rollers that roll over a flexible tube portion of an irrigation line connected to a supply of fluid for surgical or dental use;
(b) first means capable, in succession, of receiving the flexible tube portion in front of a plane in which the rollers move, then bringing the flexible tube portion underneath the rollers and then finally pressing the flexible tube portion against the rollers;
(c) a slide that defines a housing for receiving the flexible tube portion and movements of the slide are controlled by a handle, wherein the slide and the handle are both pivotally mounted about a common shaft integral with a frame of the peristaltic pump; and
(d) a large surface of the frame parallel to the plane in which the rollers move, wherein, during movement that closes the slide, the handle and the slide are first of all pivotally coupled and both pivot about the common shaft thereof until the slide abuts, via a tip of the slide, against the large surface of the frame of the peristaltic pump, wherein a base of the slide is arranged at a distance from the large surface of the frame, wherein the handle then is uncoupled from the slide and continues to pivot about the common shaft thereof, forcing the slide to make a swiveling motion that tends to return the base against the large surface of the frame of the peristaltic pump and a vertical translation motion upwards into a position in which the slide extends parallel to the large surface of the frame of the peristaltic pump.

2. The peristaltic pump according to claim 1, wherein a stud integral with the slide follows a cam path provided on the handle, and wherein the common shaft of the slide and the handle projects into the cam path provided on the slide, wherein the cam path moves relative to the common shaft.

3. The peristaltic pump according to claim 1, wherein the handle is provided with at least one arm that cooperates with a cam profile provided on the slide for temporarily pivotally coupling the slide and the handle, wherein the arm moves, via a free end thereof, into a notch provided on the frame of the peristaltic pump, when an assembly formed by the slide and the handle is in a closed position.

4. The peristaltic pump according to claim 2, wherein the handle is provided with at least one arm that cooperates with a cam profile provided on the slide for temporarily pivotally coupling the slide and the handle, wherein the arm moves, via a free end thereof, into a notch provided on the frame of the peristaltic pump, when an assembly formed by the slide and the handle is in a closed position.

5. The peristaltic pump according to claim 3, wherein the handle has a shoulder that, when the handle is in the closed position, moves under a plane surface of a cam path.

6. The peristaltic pump according to claim 4, wherein the handle has a shoulder that, when the handle is in the closed position, moves under a plane surface of the cam path.

7. The peristaltic pump according to claim 1, wherein the slide includes at least one catch, partially separated from the slide by a vertical groove and ending in a tooth, the function of which is to limit clearance of the slide, when the slide is opened or closed, wherein the catch slides into a vertical slot arranged in the large surface of the frame of the peristaltic pump, wherein the large surface of the frame projects into the vertical groove when the slide is in the closed position.

8. The peristaltic pump according to claim 2, wherein the slide includes at least one catch, partially separated from the slide by a vertical groove and ending in a tooth, the function of which is to limit clearance of the slide, when the slide is opened or closed, wherein the catch slides into a vertical slot arranged in the large surface of the frame of the peristaltic pump, wherein the large surface of the frame projects into the vertical groove when the slide is in the closed position.

9. The peristaltic pump according to claim 3, wherein the slide includes at least one catch, partially separated from the slide by a vertical groove and ending in a tooth, the function of which is to limit clearance of the slide, when the slide is opened or closed, wherein the catch slides into a vertical slot arranged in the large surface of the frame of the peristaltic pump, wherein the large surface of the frame projects into the vertical groove when the slide is in the closed position.

10. The peristaltic pump according to claim 5, wherein the slide includes at least one catch, partially separated from the slide by a vertical groove and ending in a tooth, the function of which is to limit clearance of the slide, when the slide is opened or closed, wherein the catch slides into a vertical slot arranged in the large surface of the frame of the peristaltic pump, wherein the large surface of the frame projects into the vertical groove when the slide is in the closed position.

11. A peristaltic pump including:
(a) a plurality of rollers that roll over a flexible tube portion of an irrigation line connected to a supply of fluid for surgical or dental use;
(b) first means capable, in succession, of receiving the flexible tube portion in front of a plane in which the rollers move, then bringing the flexible tube portion underneath the rollers and then finally pressing the flexible tube portion against the rollers;
(c) a slide that defines a housing for receiving the flexible tube portion and movements of the slide are controlled by a handle, wherein the slide and the handle are both pivotally mounted about a common shaft integral with a frame of the peristaltic pump, and wherein the slide and the handle form a removable assembly together with the frame of the peristaltic pump to which the slide and the handle are secured; and
(d) a large surface of the frame parallel to the plane in which the rollers move, wherein, during movement that closes the slide, the handle and the slide are first of all pivotally coupled and both pivot about the common shaft thereof until the slide abuts, via a tip of the slide, against the large surface of the frame of the peristaltic pump, wherein a base of the slide is arranged at a distance from the large surface of the frame, wherein the handle then is uncoupled from the slide and continues to pivot about the common shaft thereof, forcing the slide to make a swiveling motion that tends to return the base against the large surface of the frame of the peristaltic pump and a vertical translation motion upwards into a position in which the slide extends parallel to the large surface of the frame of the peristaltic pump.

12. The peristaltic pump according to claim 11, wherein a stud integral with the slide follows a cam path provided on the handle, and wherein the common shaft of the slide and the handle projects into the cam path provided on the slide, wherein the cam path moves relative to the common rotational shaft.

13. A flexible tube portion for an irrigation line connected to a supply of fluid for surgical or dental use, wherein the flexible tube portion is disposed to cooperate with rollers of a peristaltic pump for distributing the fluid, wherein the flexible tube portion is mounted on a support part that is also flexible and the flexible tube portion includes first means that define, between two free ends of the flexible tube portion, a distance that, combined with the length of the flexible tube portion, gives the flexible tube portion a determined profile enabling the flexible tube portion to be positioned directly underneath a raceway of the rollers of the peristaltic pump, wherein the support part is fitted with a gripping clamp including two jaws that, when pressed, bend the support part, and wherein the support part includes means for connecting the flexible tube portion both to an inlet tube through which the fluid arrives and to an outlet tube through which the fluid is expelled by the peristaltic pump, wherein the means for connecting the flexible tube portion both to the inlet tube through which the fluid arrives and to the outlet tube through which the fluid is expelled by the peristaltic pump includes
i. a ring under which the inlet tube is placed;
ii. a guide groove into which the inlet tube is disposed;
iii. a notched tip;
iv. a hole formed in a base plate of the support part, wherein the notched tip extends through the hole formed in the base plate; and
v. a crimping ring that crimps an end of the flexible tube portion to the notched tip.

* * * * *